United States Patent [19]

McGrath et al.

[11] Patent Number: 4,973,631

[45] Date of Patent: Nov. 27, 1990

[54] NOVEL PHOSPHORUS CONTAINING EPOXY NETWORKS

[75] Inventors: James E. McGrath; Attila Güngör, both of Blacksburg, Va.

[73] Assignee: Virginia Tech Intellectual Properties Inc., Blacksburg, Va.

[21] Appl. No.: 418,066

[22] Filed: Oct. 6, 1989

[51] Int. Cl.⁵ .................... G08G 59/50; G08G 59/56
[52] U.S. Cl. .................................. 525/534; 525/471; 528/108; 528/398
[58] Field of Search ............... 528/108, 398; 525/535, 525/534, 471

[56] References Cited

U.S. PATENT DOCUMENTS

| | | | |
|---|---|---|---|
| 3,415,779 | 12/1968 | Preininger et al. | 528/398 X |
| 4,072,653 | 2/1978 | Moedritzer | 528/398 X |
| 4,298,709 | 11/1981 | Ginter et al. | 528/108 X |
| 4,345,059 | 8/1982 | Fretz et al. | 528/108 X |
| 4,607,092 | 8/1986 | Johnson et al. | 528/108 |

*Primary Examiner*—Earl Neilsen
*Attorney, Agent, or Firm*—Richard P. Fennelly; Louis A. Morris

[57] ABSTRACT

Epoxy resins can be cured or crosslinked with triphenyl phosphine oxide compounds having epoxy-reactive (active hydrogen) substituents either alone or in combination with amine-terminated polyarylene ethers (e.g., amine-terminated polysulfone oligomers or high polymers.

6 Claims, No Drawings

NOVEL PHOSPHORUS CONTAINING EPOXY NETWORKS

Novel, high performance, phosphorus containing epoxy networks have been prepared and characterized using 1 as the crosslinking moiety, and also using 1 in conjunction with amine terminated polysulfones as the crosslinking reagents. These formulations are useful as flame retardant epoxy networks. They also provide a method of toughening the otherwise brittle cured materials.

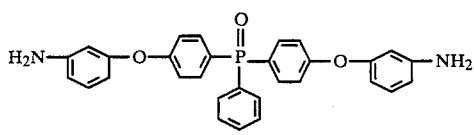
1

The chain extender 1, has been prepared according to Scheme 1 where X=Cl or F. The phosphorus dihalide monomer and aminophenol are charged to a reaction vessel equipped with an agitator, nitrogen inlet, and condenser with a Dean Stark trap for water removal. Both dimethylacetamide and toluene are previously dried over calcium hydride, distilled, and maintained under inert atmosphere. The reaction solvents, then the potassium carbonate are charged and the temperature is brought up to the reaction temperature. When X=F, optimum conditions for the reaction

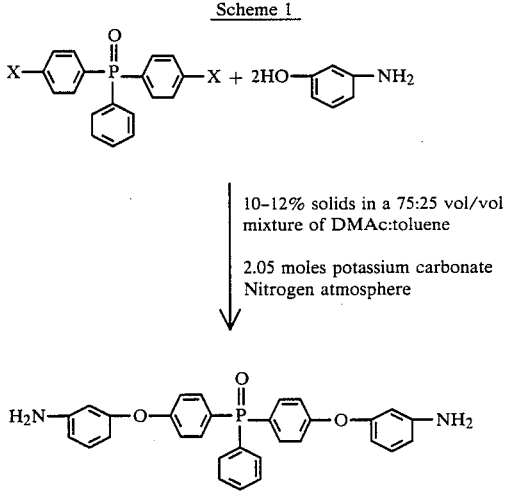

are 140° c. for a 14 hr. period. Crude yield of this reaction is ≈93%. When X=Cl, optimium conditions are 160° C. for a period of 36 hrs. and the crude yield is ≈60%. Following completion of the reaction, toluene and excess dimethylacetamide are vacuum stripped from the system until a 30-35% solution of the product in dimethylacetamide is obtained. The product crystalline in this solution over approximately a 6 hr. period. They are filtered, washed, dried at 60° C. under vacuum, then recrystallized from dimethylacetamide. Finally the recrystallized material is recovered and dried under vacuum at 150° C. t a constant weight.

The instant invention, in its broadest context, involves the use of a "triphenyl phosphine oxide epoxy curing agent" which is to be understood as encompassing compounds having the structure, for example, of

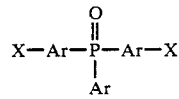

where each of the three groups is a substituted or unsubstituted phenyl ring with the proviso that such compounds also contain epoxy-reactive substitutent(s) (shown, for example, by the moieties X). As is well known in the art, such substituents X have active hydrogen and include amine (—NH$_2$), hydroxy (—OH), carboxy (—COOH), anhydride, and thiol (—SH). moieties. It is preferred that two or more such substituents reside in the compound (e.g., either directly on one or more of the Ar groups or on suitable substitutents, e.g., —OAr', on such Ar groups). The above crosslinking agent can be used with other amine terminated polymers, if desired, for example, amine-terminated polyarylene ethers such as the polysulfone oligomers or high polymers.

EXAMPLE 1

The diglycidyl ether of bisphenol-A (1.74 g) was charged to an aluminum mold and preheated to ≈80° C. This was degassed under vacuum at 100° C. for 5 minutes. Monomer 1 (1.26 g) was then charged to the mold. This mixture was agitated, then degassed a second time. The mold was brought to curing temperature, 150° C., and maintained at that temperature for 45 minutes, then, subsequently, the temperature was raised to 190° C. and maintained at this temperature for an additional 45 minutes. The sample was cooled slowly to room temperature to produce a transparent, light yellow-green material.

EXAMPLE 2

Preparation of a cured epoxy material containing both an aromatic amine terminated polyarylether sulfone oligome: of 16,000 g/mole (15 weight % of the final cured material) and the phosphorus containing curing reagent, 1: 0.3 g of the aromatic amine terminated polyarylether sulfone and 0.98 g of the diglycidyl ether of bisphenol-A were charged to an aluminum mold. This mixture was preheated to 100° C., then agitated until homogeneity was complete (≈25 minutes). The mixture was than degassed under vacuum at 100° C. 0.71 g of the phosphorus containing curing agent, 1, was charged and the mixture was agitated to attain a homogeneous solution, and subsequently, degassed at 100° C. a second time (10 minutes). Curing was effected by heating at 150° C. for 45 minutes, then at 190° C. for an additional 45 minutes. The sample was cooled slowly to room temperature to produce a transparent, light yellow-green material.

EXAMPLE 3

Preparation of a cured epoxy material containing both an aromatic amine terminated polyarylether sulfone oligomer of 16,000 g/mole (30% by weight of the final material) and the phosphorus containing curing reagent, 1: 0.6 g of the aromatic amine termianted polyarylether sulfone and 0.8 g of the diglycidyl ether of bisphenol-A were charged to an aluminum mold. This mixture was preheated to 100° C., then agitatedf intil homogeneity was complete (≈25 minutes). The mixture was than degassed under vacuum at 100° C. 0.58 g of the phosphorus containing curing agent,1, was charged and the mixture was agitated to attain a homogeneous solution, and subsequently, degassed at 100° C. a second time (10 minutes). Curing was effected by heating at 150° C. for 45 minutes, then at 190° C. for an additional 45 minutes. The sample was cooled slowly to room temperature to produce a transparent, light yellow-green material.

For the 15 weight percent polyarylether sulfone containing phosphene-epoxy material, samples were freeze-fractured and scanning electron photomicrographs were taken of the fracture surfaces. These micrographs indicate that an epoxy matrix is present containing polysulfone domains of $\approx 0.8$-$1$ $\mu$ in diameter. The 30 weight percent polyarylether sulfone containing material was subjected to the same type of analysis. In these samples, the photomicrographs indicate that phase inversion has occured. Thus, epoxy domains of 1.5–2.0 $\mu$ are present in a thin matrix of the polyarylether sulfone component.

Differential scanning calorimetry data performed at 10°/minute on the phosphone-epoxy material without any added polyarylether sulfone component, shows a glass transition of 170° C.

We claim:

1. A curable epoxy resin composition containing a curable epoxy resin and, as a curing agent, an effective amount for curing of a triphenyl phosphine oxide epoxy curing agent substitured with an active hydrogen substituent.

2. A composition as claimed in claim 1 wherein the active hydrogen substituent is —$NH_2$.

3. A composition as claimed in claim 1 wherein at least two active hydrogen substituents are contained in the curing agent.

4. A composition as claimed in claim 2 wherein the active hydrogen substituent is —$OC_6H_5NH_2$.

5. A composition as claimed in claim 4 wherein the curing agent is 4,4'-[(phenylphosphinylidene)bis(4,1-phenyleneoxy)]bis-benzenamine.

6. A composition as claimed in claim 1 which further comprises an amine-terminated polysulfone oligomer or high polymer.

* * * * *